(12) United States Patent
Tham

(10) Patent No.: US 7,113,313 B2
(45) Date of Patent: Sep. 26, 2006

(54) DOME-SHAPED APPARATUS FOR INSPECTING A COMPONENT OR A PRINTED CIRCUIT BOARD DEVICE

(75) Inventor: Yew Fei Tham, Singapore (SG)

(73) Assignee: Agilent Technologies, Inc., Palo Alto, CA (US)

( * ) Notice: Subject to any disclaimer, the term of this patent is extended or adjusted under 35 U.S.C. 154(b) by 903 days.

(21) Appl. No.: 10/161,885

(22) Filed: Jun. 3, 2002

(65) Prior Publication Data

US 2002/0196338 A1 Dec. 26, 2002

(30) Foreign Application Priority Data

Jun. 4, 2001 (SG) .............................. 200103257-2

(51) Int. Cl.
*H04N 1/04* (2006.01)
(52) U.S. Cl. ...................... 358/474; 358/475; 358/509; 358/514; 250/558; 250/572
(58) Field of Classification Search ................ 358/474, 358/475, 509, 514; 250/558, 572
See application file for complete search history.

(56) References Cited

U.S. PATENT DOCUMENTS

| | | | |
|---|---|---|---|
| 4,677,473 A | | 6/1987 | Okamoto et al. |
| 5,017,864 A | * | 5/1991 | Kaida et al. ................. 324/754 |
| 5,039,868 A | * | 8/1991 | Kobayashi et al. .... 250/559.08 |
| 5,060,065 A | * | 10/1991 | Wasserman ................. 348/131 |
| 6,762,847 B1 | * | 7/2004 | Duquette et al. ........... 356/614 |

* cited by examiner

*Primary Examiner*—Douglas Q. Tran
*Assistant Examiner*—Negussie Worku

(57) ABSTRACT

An apparatus for inspecting a printed circuit board device, the device including at least one component mounted on a circuit board, the apparatus comprising an object carrier for carrying the printed circuit board device, imaging means for imaging along an optical axis so as to receive light reflected from surfaces of the device when placed on the object carrier within a field of view of the imaging means, and light projecting means for projecting light toward the object carrier in an oblique direction with respect to the optical axis of the imaging means for illumination of said surfaces of the device. The light projecting means includes a substantially dome-shaped structure incorporating a plurality of light elements for producing and projecting the light. Said plurality of light elements includes light elements of different light characteristics and light elements of different orientations of projection for creating a predetermined illumination pattern on said surfaces of said printed circuit board device. The dome-shaped structure is composed of an assembly of a plurality of structural rings, each incorporating an array of said light elements and being fitted together in an replaceable manner to form said ring assembly, thereby enabling to vary said light pattern by replacing one or more of said structural rings that are incorporating light elements of predetermined light characteristics and predetermined orientation of projection by different structural rings incorporating light elements of different light characteristics and orientation of projection than said predetermined ones.

7 Claims, 3 Drawing Sheets

DOME-SHAPED APPARATUS FOR INSPECTING A COMPONENT OR A PRINTED CIRCUIT BOARD DEVICE

BACKGROUND OF THE INVENTION

The present invention relates to an apparatus for inspecting a component or a printed circuit board device.

Apparatus for inspecting a printed circuit board device enables a variety of features of a printed circuit board device to be inspected including, for example, the quality of solder joints and the placement and different features of the components. During inspection of solder joints, defects can be detected and categorized into defect types, such as solder bridging or shorting, no solder, insufficient solder, de-wetted solder, void in solder, excessive solder, and tombstoning. The types of defects which can occur in the placement and with regard to the features of components include amongst others wrong orientation or polarity of the component, misalignment of the component, missing component, incorrect component type, wrong component value, wrong component marking, and inverted component.

There are major differences between the visual appearance of solder joints and the visual appearance of components. Typically, solder joints are highly reflective (shiny) and posses certain distinguishable three-dimensional shapes, whereas the visual appearance of components is characterized by large variations in color, surface texture, shape, and height. Components also tend to include identification markings, which can vary widely, to represent features such as polarity, orientation, value, part number and so on. Some polarity identifications are represented by a color, a bar, a dimple, or characters. Laser marking is an increasingly popular method of generating identification markings on components.

In prior art apparatus for inspecting a printed circuit board device, various colors will correspond to images produced at different elevations relative to the printed circuit board under inspection to produce a mapping which constitutes a three dimensional representation of a two dimensional image providing a significantly enhanced image for visual inspection purposes. By analyzing the smoothness of the transitions from one topographical zone to the next, a measure of solder wetting can be made. By detecting aberrations or secondary shapes, voids, blow holes and pinholes may be detected. Thus, significant information may be developed by performing weighted calculations.

U.S. Pat. No. 5,039,868 discloses a substrate inspection apparatus comprising light projecting means including a plurality of ring-shaped sources for directing light of different hues to a part obliquely from one direction at different angles of incidence, first imaging means including a color camera for imaging reflected light from the surface of a portion to be inspected by hues on the center line of each of the right-shaped light sources in a position directly over the part. There is no provision to independently control each of the light sources.

U.S. Pat. No. 4,677,473 describes a soldering inspection system wherein light is irradiated on a soldered part at different incident angles by a light emitting means to collect information indicative of three-dimensional configuration of the soldered part and discriminate whether or not the configuration is acceptable. The three-dimensional configurational information can be obtained with light irradiated at least from two positions mutually of different angles with respect to the soldered part. The inspection is thereby made from a quantitative viewpoint.

U.S. Pat. No. 5,060,065 discloses a printed circuit board inspection device including a lighting system for use with a series of cameras associated with the inspection device, the lighting system being essentially domed in configuration and incorporating a plurality of selectively controllable light emitting diodes for developing desired lighting patterns. The light emitting diodes are arranged within the domed fixture to form an array of defined latitudes and longitudes and are capable of selective activation to develop the particular lighting patterns which are desired. This permits acquisition of images useful in developing a "topographical display" of the acquired image, which is useful in enhancing the subsequent inspections which are to be performed. The domed fixture is integrally formed and has a predetermined arrangement of light elements of different light characteristics and orientations of projection for creating a predetermined illumination pattern. Therefore, different models of domed fixtures need to be manufactured for different applications, and the whole domed fixture has to be replaced for another application.

SUMMARY OF THE INVENTION

According to a first aspect of the present invention, there is provided a dome-shaped illumination assembly for illuminating a component under inspection, comprising a plurality of rings of different diameter, the rings being stacked on top of each other in order of decreasing diameter, wherein each ring comprises a plurality of light sources for illuminating the component under inspection.

An assembly in accordance with the first aspect of the present invention has the advantage that a ring in the assembly can easily be swapped with another ring of the same diameter but containing different light sources. Thus the configuration of the light sources can be varied in a simple and effective manner by swapping rings in the assembly.

According to a second aspect of the present invention, there is provided an apparatus for inspecting a printed circuit board device, the device including at least one component mounted on a circuit board, the apparatus comprising an object carrier for carrying the printed circuit board device, imaging means for imaging along an optical axis so as to receive light reflected from surfaces of the device when placed on the object carrier within a field of view of the imaging means, and light projecting means for projecting light toward the object carrier in an oblique direction with respect to the optical axis of the imaging means for illumination of said surfaces of the device. The light projecting means includes a substantially dome-shaped structure incorporating a plurality of light elements for producing and projecting the light. Said plurality of light elements includes light elements of different light characteristics and light elements of different orientations of projection for creating a predetermined illumination pattern on said surfaces of said printed circuit board device. The dome-shaped structure is composed of an assembly of a plurality of structural rings, each incorporating an array of said light elements and being fitted together in replaceable manner to form said ring assembly, thereby enabling a user to vary said light pattern by replacing one or more of said structural rings that are incorporating light elements of predetermined light characteristics and predetermined orientation of projection by different structural rings incorporating light elements of different light characteristics and orientation of projection than said predetermined ones.

By providing said ring assembly it is possible to individually replace each of said structural rings incorporating said light elements of predetermined light characteristics and orientations of projection. Different light characteristics may be realized by different colors or different light intensities emitted by the respective light elements. Different orientation of projection may be realized by different angles between the optical axis of the dome shaped structure and the axis of the light beam emitted by the respective light elements. The color and angle of orientation of each of the light elements can be selected independently for each of said rings. All the different rings can be precisely fitted on top of each other and locked by a simple locking mechanism. According to the invention, the dome-shaped structure is of a construction which is flexible for variations, wherein each structural ring can be easily and economically manufactured and reconfigured to change the dome-shaped structure for different applications.

Thus, an apparatus for inspecting a printed circuit board device in accordance with the second aspect of the invention has the advantage that the configuration of the light elements regarding light characteristics and orientations of projection can be easily varied and modified without replacing the whole dome structure so that the costs for manufacturing and maintenance can be reduced.

DETAILED DESCRIPTION OF THE INVENTION

Preferred embodiments of the present invention will now be described with reference to the attached drawings.

Figure 1:
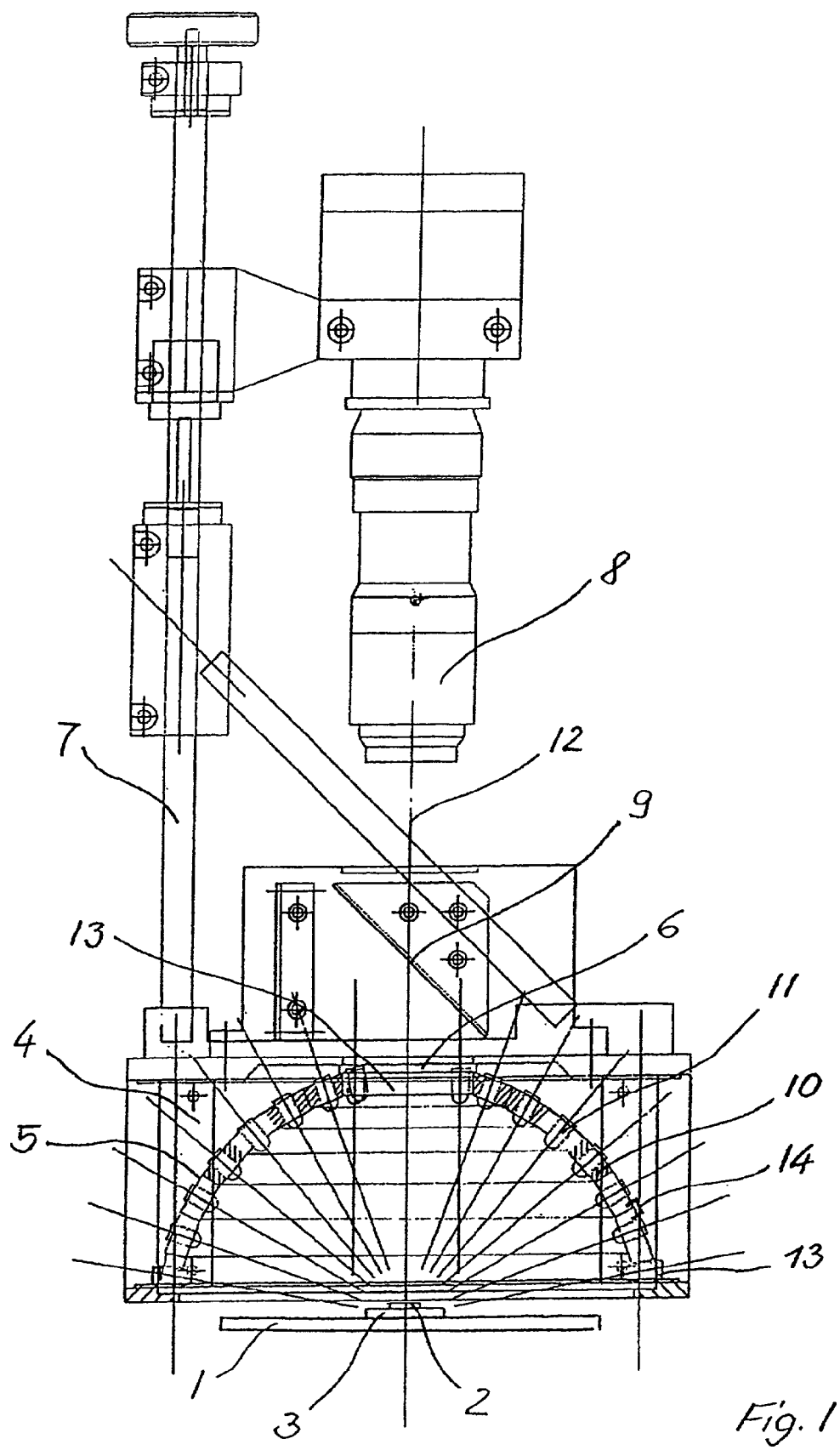
FIG. 1 is a side view of an apparatus for inspecting a printed circuit board device according to an embodiment of the present invention.

FIG. 1 shows an apparatus for inspecting a printed circuit board device according to an embodiment of the present invention. The apparatus comprises an object carrier 1 which carries the printed circuit board device including a component 2 mounted on a circuit board 3. The object carrier 1 carrying the printed circuit board device is displaceable in horizontal directions of an x,y-coordinates system. The apparatus further comprises a base 4 fixedly disposed above the object carrier 1. The base 4 horizontally carries a dome-shaped lightening structure 5 facing downwards with its concave inner surface and having an opening 6 in the center of its top. A column 7 is vertically mounted on the base 4, wherein a multi-channel color video camera 8 is mounted to the column 7 so as to be focused in a vertical direction toward and through the opening 6 in the top of the dome-shaped structure 5. A half-transparent beam splitting mirror 9 is mounted on the column 7 in an oblique direction between the video camera 8 and the top of the dome-shaped structure 5.

The dome-shaped structure 5 of concave configuration is composed of an assembly of a plurality of structural rings 10 of different diameters, each of the structure rings 10 incorporating, at the radially inner faces thereof, a plurality of light elements 11 of different light characteristics and orientations of projections. The structure rings 10 are precisely fitted together to form a ring assembly. The light elements 11 produce and project the light downwardly in an oblique (radial) direction with respect to an optical axis 12 of the video camera 8 toward the center of the concave dome-shaped structure 5 to create a predetermined illumination pattern on the surfaces of the component 2 on the circuit board 3. When the component 2 is placed on the object carrier 1 within a field of view of the video camera 8, the light reflected from surfaces of the component 2 on the circuit board 3 is received via the mirror 9 by the video camera 8 along the optical axis 12.

The light elements 11 may be light emitting diodes (LED) or fiber optics and may produce light of different colors or light intensities. Additionally, the light elements 11 may project in different radial orientations with respect to the dome-shaped structure so that the combination of light elements of different light characteristics and light elements of different orientations of projection results in a predetermined illumination pattern on the surfaces of the component 2. The light elements 11 may be independently controlled on the several structural rings 10. As an example, light elements 11 of some of rings 10 may emit light of red color, others may emit light of yellow or blue color of even of mixed colors such as white color.

For different applications, the configuration of the ring assembly may be easily modified, thereby enabling a user to vary the light pattern by replacing a number of the structural rings 10 that incorporate light elements 11 of predetermined light characteristics and predetermined orientation of projection by different structural rings 10 incorporating light elements 11 of different light characteristics and orientation of projection than said predetermined ones. For example, rings 10 incorporating or carrying light elements emitting a red color may be replaced by rings 10 incorporating or carrying light elements emitting a white color, or some rings 10 having light elements 11 of a certain light intensity may be replaced by other rings 10 equipped with light elements 11 of a reduced or increased light intensity. By replacing the individual rings 10 it is possible to easily change the dome-shaped structure 5 without replacing the whole dome-shaped structure 5.

Preferably, the dome-shaped structure 5 may have a hollow hemispherical shape, wherein the structural rings 10 are stacked on top of each other in parallel to the object carrier 1. This enables the dome-shaped structure 5 to be symmetrically arranged relative to the optical axis 12, so that a precise inspecting of the printed circuit board device is guaranteed. Alternatively, the dome-shaped structure 5 may have a shape other than the hemispherical shape, if a special illumination pattern should be created by a particular orientation of projection of the light elements 11 for a special application.

In a preferred embodiment of the present invention, a locking mechanism is provided for locking the ring assembly of the dome-shaped structure 5. The locking mechanism comprises ring-shaped flanges 13 arranged on the bottom and on top of the ring assembly, as shown in FIG. 1. By arranging the ring-shaped flanges 13 it is possible to stably fit the structural rings 10 in the ring assembly and reliably hold all the individual rings 10 together. The ring assembly also may be clamped together by clamping means 14, such as hooks or the like, to precisely fit the individual rings 10 together.

Figure 2:
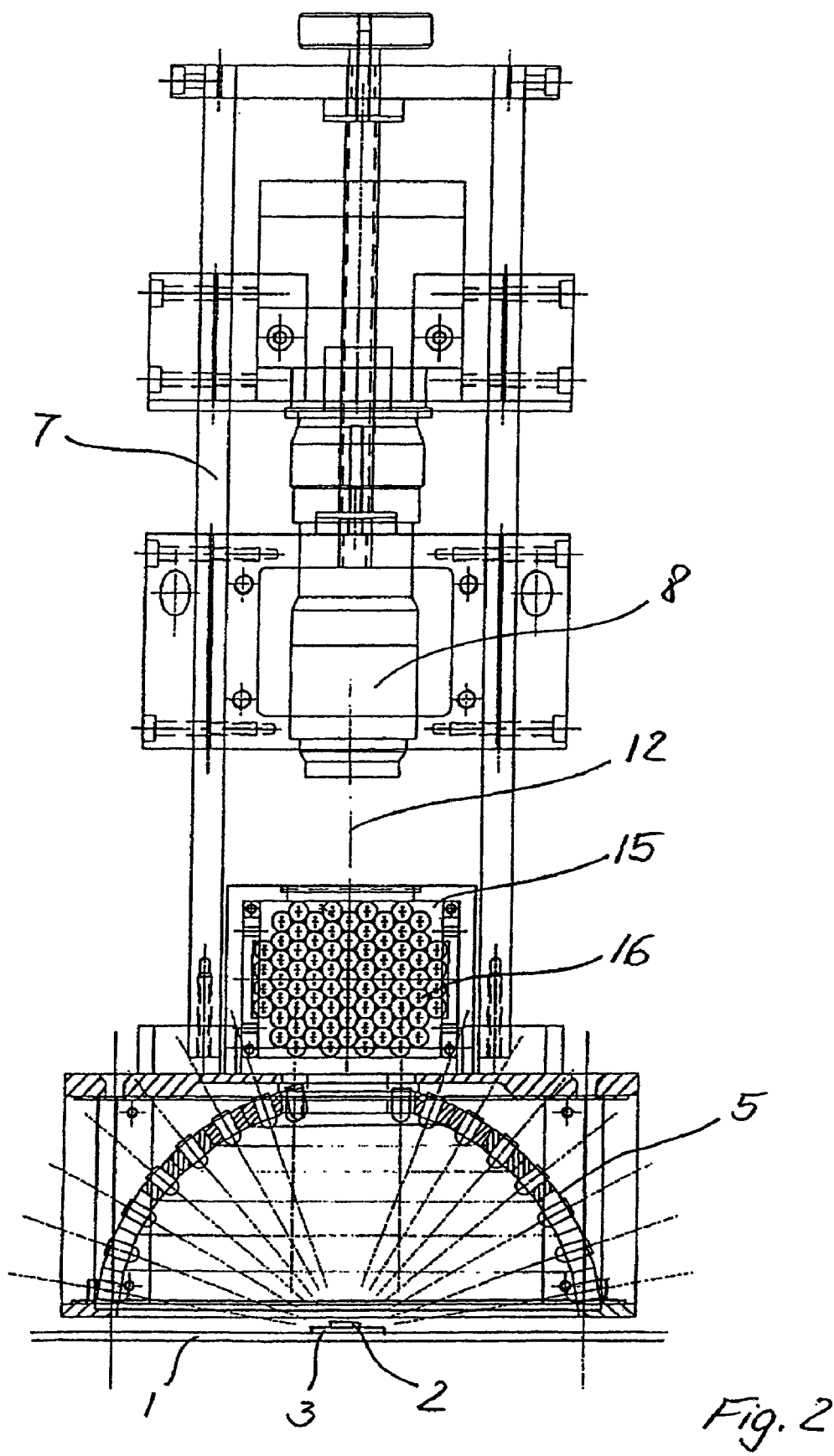
FIG. 2 is a side view of an apparatus for inspecting a printed circuit board device according to another embodiment of the present invention.

FIG. 2 shows an apparatus for inspecting a printed circuit board device according to another embodiment of the present invention. In this embodiment, the video camera 8 is displaceable on the column 7 in a vertical direction. Further, a plane-shaped lighting fixture 15 incorporating a plurality of light emitting diodes 16 of different intensity is mounted on the column 7 between the video camera 8 and the dome-shaped structure 5. The light emitting diodes 16 of the lighting fixture 15 enable background illumination of the surfaces of the component 2 of the circuit board 3 carried by the object carrier 1. Therefore, further predetermined illumination pattern on the surfaces of the component 2 of the circuit board 3 may be created for imaging by the video camera 8 along the optical axis 12.

Figure 3:
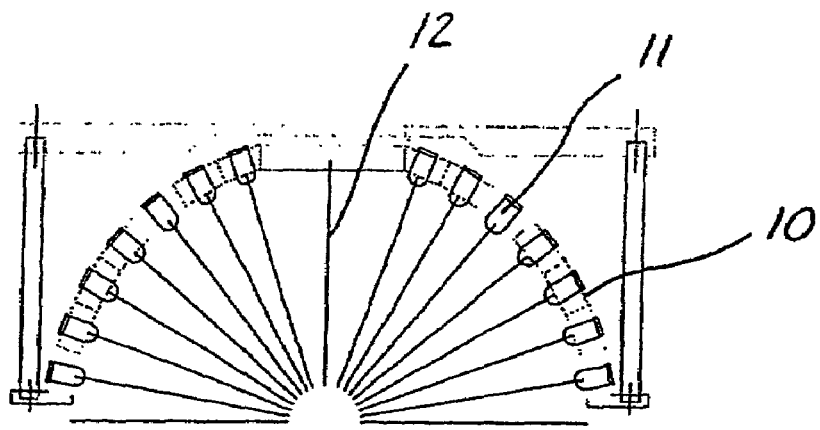
FIG. 3 is a side view of a dome-shaped structure of the apparatus shown in FIG. 1.
Figure 4:
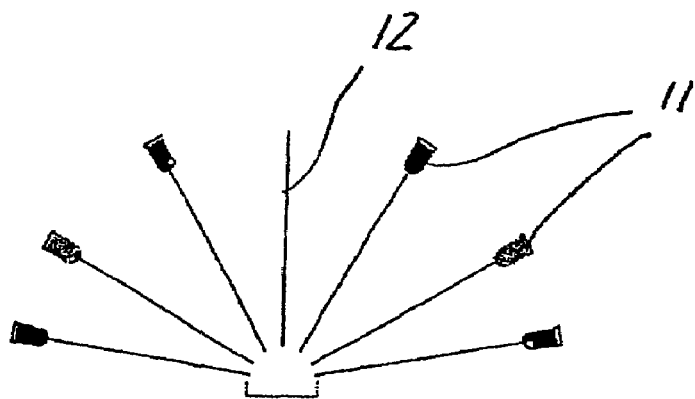
FIG. 4 is a side view of an arrangement of light elements with predetermined light characteristics and orientations of projection.

As shown in FIGS. 3 and 4, the structural rings 10 of the ring assembly are disposed such that the light elements 11 have a predetermined orientation of projection and a predetermined color, respectively. As shown in FIG. 3, the light elements 11 project light in an oblique direction with respect to the optical axis 12 in a predetermined angle. As shown in FIG. 4, the light elements 11 have different colors and are disposed at a predetermined angle with respect to the optical axis 12.

Figure 5:
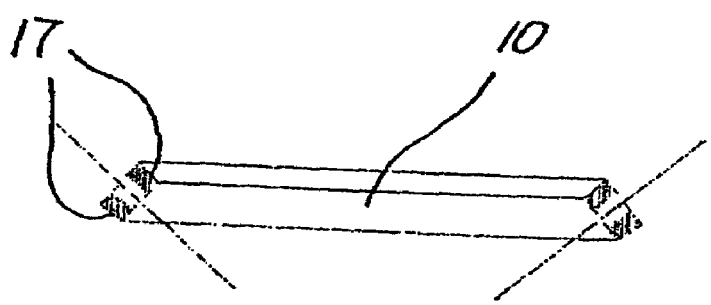
FIG. 5 is a cross-section view of a structural ring of the ring assembly according to the invention.

FIG. 5 shows a cross-sectional view of a single structural ring 10 of the ring assembly of the dome-shaped structure 5 according to the present invention. The structural ring 10 includes side surfaces 17 and has a spline-shaped section so that the side surfaces 17 of the structural ring 10 are inclined in a radial direction. By providing the spline-shaped section of the structural ring 10, the ring assembly may be precisely fitted together so that a reliable self-locking of the structural rings 10 is possible. A structural ring 10 having such a shape can be manufactured easily and economically. Though the radially inner faces of the rings are shown to be conical and be plane in cross-section, the inner faces may be sections of a sphere having a radius of curvature of the hemispherical inner shape of dome-shaped structure 5.

As described, apparatus according to the invention is used to inspect a printed circuit board device arranged on an object carrier of the apparatus. However, it should be noted that apparatus according to the invention can also be utilized to inspect a variety of features, e.g. surface characteristics, of other electrical and electronic components and substrates, such as single electronic components, leadframes, ball grid array substrates, etc. Such components and substrates may or may not be placed on an object carrier of the apparatus.

While the preferred embodiments of the invention has been described, they are merely illustrative of the principles of the invention. Other embodiments and configurations may be devised without departing from the scope of the appended claims.

What is claimed is:

1. An apparatus for inspecting a printed circuit board device having a component, the apparatus comprising an object carrier for carrying the printed circuit board device, imaging means for imaging along an optical axis so as to receive light reflected from surfaces of the device when placed on the object carrier within a field of view of the imaging means, and light projecting means for projecting light toward the object carrier in an oblique direction with respect to the optical axis of the imaging means for illumination of said surfaces of the device, the light projecting means including a substantially dome-shaped structure incorporating a plurality of light elements for producing and projecting the light, said plurality of light elements including light elements of different light characteristics and light elements of different orientations of projection for creating a predetermined illumination pattern on said surfaces of said printed circuit board device, wherein said dome-shaped structure is composed of an assembly of a plurality of structural rings incorporating said light elements and being fitted together in a replaceable manner to form said ring assembly, thereby enabling said light pattern to be varied by replacing one of said structural rings that incorporates light elements of predetermined light characteristics and predetermined orientation of projection by a different structural ring incorporating light elements of different light characteristics and orientation of projection.

2. The apparatus according to claim 1, wherein said light elements of different light characteristics include light elements producing light of different colors.

3. The apparatus according to claim 1, wherein said light elements comprise light emitting diodes (LED).

4. The apparatus according to claim 1, wherein said rings include side surfaces and have spline-shaped cross sections such that the side surfaces of the rings are inclined in radial directions.

5. The apparatus according to claim 1, wherein said rings are stacked on top of each other in parallel to the object carrier.

6. The apparatus according to claim 1, further comprising a locking mechanism for locking the ring assembly, the locking mechanism being formed as ring-shaped flanges arranged on the ring assembly.

7. The apparatus according to claim 1, further comprising clamping means for clamping together the ring assembly.

* * * * *